United States Patent [19]

Kawai et al.

[11] Patent Number: 4,523,041

[45] Date of Patent: Jun. 11, 1985

[54] METHOD OF PURIFYING 4-FLUOROPHENOL

[75] Inventors: Toshikazu Kawai, Kawagoe; Haruo Suzuki, Tokyo; Shouzou Kaneda, Kawagoe, all of Japan

[73] Assignee: Central Glass Company, Limited, Ube, Japan

[21] Appl. No.: 614,047

[22] Filed: May 25, 1984

[30] Foreign Application Priority Data

Jun. 23, 1983 [JP] Japan .............................. 58-111819

[51] Int. Cl.$^3$ .................... C07C 37/86; C07C 37/68
[52] U.S. Cl. .................................... 568/755; 568/775
[58] Field of Search .............................. 568/755, 775

[56] References Cited

U.S. PATENT DOCUMENTS 2,934,569  4/1960  Kuchlewind ....................... 568/775
2,950,325  8/1960  Britton et al. ..................... 568/755

FOREIGN PATENT DOCUMENTS 12669  8/1962  Japan ............................... 568/775

OTHER PUBLICATIONS

"J. Organic Chem.", vol. 26, (1961) p. 4641.

Primary Examiner—Werren B. Lone
Attorney, Agent, or Firm—Schwartz, Jeffery, Schwaab, Mack, Blumenthal & Evans

[57] ABSTRACT

A method of efficiently purifying crude 4-fluorophenol containing phenol as impurity. Phthalic acid or its anhydride, or a suitable derivative of phthalic acid, and a dehydrating agent such as sulfuric acid or a metal chloride are mixed with the crude 4-fluorophenol, and the mixture is kept in a liquid state usually with moderate heating to 30°–180° C. until completion of condensation reaction between phenol and the phthal-compound. After that pure 4-fluorophenol can easily be recovered by distillation or recrystallization.

7 Claims, No Drawings

METHOD OF PURIFYING 4-FLUOROPHENOL

BACKGROUND OF THE INVENTION

This invention relates to a method of purifying crude 4-fluorophenol containing phenol as impurity.

4-Fluorophenol is a compound known as an intermediate material for the preparation of some medicines and agricultural chemicals.

As described in J. Org. Chem., 26, 4641 (1961), 4-fluorophenol can be synthesized with comparatively good yields by alkaline hydrolysis of 4-bromofluorobenzene under superatmospheric pressure conditions. However, it is inevitable that 4-fluorophenol obtained by this method is contaminated with phenol which is formed as a by-product, and it is very difficult to isolate 4-fluorophenol from the crude product by reason of very close resemblances between this compound and phenol in their physical properties. That is, phenol cannot completely be separated from 4-fluorophenol even by superfractionation.

Another known method for the synthesis of 4-fluorophenol is the reaction of phenol with elemental fluorine in a suitable solvent such as aqueous hydrogen fluoride, but this fluorination reaction is very low in selectivity so that considerable amounts of 2-fluorophenol and 2,4-difluorophenol are formed together with 4-fluorophenol. Also in this case, 4-fluorophenol is likely to be contaminated with phenol remaining unreacted. It is also known that 4-fluorophenol can be obtained by hydrolysis of a diazonium salt of 4-aminophenol. However, in this case the yields are too low for industrial practice.

Under such circumstances, there is a keen demand for an efficient method of purifying 4-fluorophenol contaminated with phenol.

SUMMARY OF THE INVENTION

It is an object of the present invention to provide an efficient and industrially practicable method of purifying crude 4-fluorophenol containing phenol as impurity.

To accomplish this object there is provided a method of purifying crude 4-fluorophenol containing phenol as impurity, the method comprising the steps of adding a phthal-compound which readily reacts with phenol but hardly reacts with 4-fluorophenol and a dehydrating agent to the crude 4-fluorophenol to obtain a mixture, keeping the mixture in a liquid state until substantial completion of the reaction between phenol coexisting with 4-fluorophenol and the phthal-compound, and recovering 4-fluorophenol from the mixture containing the products of the aforementioned reaction.

The phthal-compound for use in this method is selected from phthalic acid, phthalic anhydride, derivatives of phthalic acid produced by nuclear substitution and their anhydrides. Preferred examples of such phthalic derivatives are chlorophthalic acid, fluorophthalic acid, methylphthalic acid, nitrophthalic acid and o-sulfobenzoic acid. The reaction between phenol and the phthal-compound is a condensation reaction represented by the following equation, where the phthal-compound is phthalic anhydride.

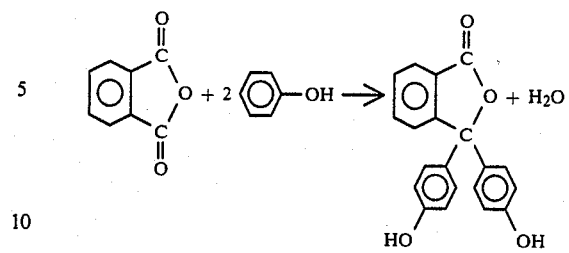

As will be understood from the equation, it is necessary to use at least 0.5 mole of a phthal-compound per 1 mole of phenol present in the crude 4-fluorophenol, and there arises no problem by using some excess of the phthal-compound.

We have confirmed that the presence of a dehydrating agent is essential for smooth proceeding and completion of the reaction between phenol and the phthal-ompound.

After completion of the reaction, pure 4-fluorophenol can easily be recovered by distillation, which may optionally be preceded by organic solvent extraction and concentration of the obtained solution, or by recrystallization.

By the method according to the invention it is possible to remove practically the entire amount of phenol contained in the crude 4-fluorophenol, and the recovery of 4-fluorophenol can be accomplished to a very high degree, such as about 95%.

DESCRIPTION OF THE PREFERRED EMBODIMENTS

The dehydrating agent in our purifying method can be selected from a variety of compounds having dehydrating ability. It is convenient and economically favorable to use either sulfuric acid or a metal halide which belongs among Lewis acids, such as zinc chloride, zinc bromide, aluminum chloride, iron chloride or tin chloride. Alternatively, use may be made of phosphorus pentoxide, polyphosphoric acid or toluenesulfonic acid. There is no strict limitation to the amount of the dehydrating agent. Usually it is suitable that the dehydrating agent amounts to 10-200% by weight of the phthal-compound, but no problem arises by using a larger amount of dehydrating agent.

To accomplish complete reaction of phenol existing as impurity with the phthal-compound, the mixture of the crude 4-fluorophenol, phthal-compound and dehydrating agent must be kept in a liquid state for a sufficient period of time. Considering the melting point (46°-51° C.) and boiling point (183°-185° C.) of 4-fluorophenol, it is suitable to moderately heat the mixture so as to keep the mixture at temperatures in the range from 30° to 180° C. until completion of the reaction described hereinbefore. The heating temperature will be determined with consideration of the kinds of the employed phthal-compound and dehydrating agent too. When a solid dehydrating agent is employed, it is optional to add an unreactive organic solvent, such as a completely substituted chlorofluoroethane, to the aforementioned mixture.

The reaction can be judged to have reached completion when sampling analysis of the mixture by gas chromatography reveals complete disappearance of phenol.

For recovery of pure 4-fluorophenol, use can be made of a commonly used organic solvent such as ether, n-hexane, ethyl acetate or methylene chloride by way of example.

The invention will further be illustrated by the following nonlimitative examples.

EXAMPLE 1

To purify crude 4-fluorophenol containing 6.3% by weight of phenol, 0.32 g of phthalic anhydride and 1.0 g of concentrated sulfuric acid were mixed with 5.34 g of the crude 4-fluorophenol. The mixture was heated to 40° C. with stirring to become liquid, and the liquid mixture was maintained at 40° C. for 1 hr with continuous stirring. After that the mixture was left to cool to room temperature.

The thus treated mixture was dissolved in 20 ml of ethyl ether by a usual extraction method to leave a small amount of insoluble matter. From the ether solution, 4.75 g of pure 4-fluorophenol having a boiling point of 183° C. was recovered by simple distillation preceded by vaporization of ether. Accordingly the recovery of 4-fluorophenol was 95%, and the degree of removal of phenol was 100%.

EXAMPLE 2

To purify crude 4-fluorophenol containing 2.0% by weight of phenol, 0.20 g of phthalic anhydride and 0.3 g of zinc chloride were mixed with 5.10 g of the crude 4-fluorophenol. The mixture was heated to 130° C. to become liquid and maintained at this temperature for 2 hr. After that the mixture was left to cool to room temperature.

The thus treated mixture was subjected to distillation under reduced pressure to obtain 4.75 g of pure 4-fluorophenol which had a boiling point of 93° C. at 25 mmHg. Accordingly the recovery of 4-fluorophenol was 95%, and the degree of removal of phenol was 100%.

EXAMPLE 3

In this case 0.5 g of tetrachlorophthalic anhydride and 0.5 g of tin tetrachloride were mixed with 5.10 g of crude 4-fluorophenol containing 2.0% by weight of phenol. The mixture was heated to 150° C. to become liquid and maintained at this temperature for 5 hr. After that the mixture was left to cool to room temperature. From the thus treated mixture, pure 4-fluorophenol was recovered by the same recovery process as in Example 1. In this case the recovery of 4-fluorophenol was calculated to be 94%, and the degree of removal of phenol was 100%.

EXAMPLE 4

In this case 0.5 g of o-sulfobenzoic acid anhydride and 0.5 g of concentrated sulfuric acid were mixed with 5.10 g of crude 4-fluorophenol containing 2.0% by weight of phenol. The mixture was heated to 100° C. to become liquid and maintained at this temperature for 2 hr with continuous stirring. After that the mixture was left to cool to room temperature. From the thus treated mixture, pure 4-fluorophenol was recovered by the same recovery process as in Example 1. In this case the recovery of 4-fluorophenol was calculated to be 95%, and the degree of removal of phenol was 100%.

What is claimed is:

1. A method of purifying crude 4-fluorophenol containing phenol as impurity, the method comprising the steps of:
    adding a phthal-compound which readily reacts with phenol but hardly reacts with 4-fluorophenol and a dehydrating agent to the crude 4-fluorophenol to obtain a mixture;
    keeping said mixture in a liquid state until substantial completion of the reaction between said phenol and said phthal-compound; and
    recovering 4-fluorophenol from the mixture containing the products of said reaction.

2. A method according to claim 1, wherein said phthal-compound is selected from the group consisting of phthalic acid, chlorophthalic acid, fluorophthalic acid, methylphthalic acid, nitrophthalic acid, o-sulfobenzoic acid and their anhydrides.

3. A method according to claim 2, wherein the amount of said phthal-compound is at least 0.5 mole per 1 mole of said phenol.

4. A method according to claim 3, wherein said dehydrating agent is selected from the group consisting of sulfuric acid, zinc chloride, zinc bromide, aluminum chloride, iron chloride, tin chloride, phosphorus pentoxide, polyphosphoric acid and toluenesulfonic acid.

5. A method according to claim 4, wherein said dehydrating agent amounts to 10–200% by weight of said phthal-compound.

6. A method according to claim 1, wherein said mixture is kept heated at temperatures in the range from 30° to 180° C. until completion of said reaction.

7. A method according to claim 1, wherein an unreactive organic solvent is added to said mixture in the initial step.

* * * * *